(12) United States Patent
Juhi

(10) Patent No.: US 6,504,157 B2
(45) Date of Patent: *Jan. 7, 2003

(54) SINGLE PHOTON EMISSION COMPUTED TOMOGRAPHY SYSTEM

(76) Inventor: Jack E. Juhi, 25595 York St., Royal Oak, MI (US) 48067

( * ) Notice: Subject to any disclaimer, the term of this patent is extended or adjusted under 35 U.S.C. 154(b) by 0 days.

This patent is subject to a terminal disclaimer.

(21) Appl. No.: 10/109,201

(22) Filed: Mar. 28, 2002

(65) Prior Publication Data

US 2002/0171041 A1 Nov. 21, 2002

Related U.S. Application Data

(63) Continuation of application No. 09/549,435, filed on Apr. 14, 2000.
(60) Provisional application No. 60/151,378, filed on Aug. 30, 1999, and provisional application No. 60/129,239, filed on Apr. 14, 2000.

(51) Int. Cl.$^7$ .............................................. G01T 1/166
(52) U.S. Cl. .............................. 250/363.04; 250/363.03
(58) Field of Search ..................... 250/363.04, 363.03, 250/363.05, 363.08, 363.09, 363.1; 378/11

(56) References Cited

U.S. PATENT DOCUMENTS

| 4,821,304 A | 4/1989 | Danos ........................... 378/86 |
| 4,937,453 A | 6/1990 | Nelson ................... 250/370.09 |
| 5,225,980 A * | 7/1993 | Hsieh et al. ............ 364/413.14 |
| 5,600,144 A | 2/1997 | Worstell |
| 5,600,145 A | 2/1997 | Plummer |
| 5,608,221 A | 3/1997 | Bertelsen et al. |
| 5,821,541 A | 10/1998 | Tumer |
| 5,825,031 A | 10/1998 | Wong |
| 5,838,009 A | 11/1998 | Plummer et al. ....... 250/363.05 |
| 5,841,140 A | 11/1998 | McCroskey et al. |
| 6,040,580 A | 3/2000 | Watson et al. ......... 250/363.03 |
| 6,147,352 A | 11/2000 | Ashburn ................ 250/363.05 |

OTHER PUBLICATIONS

IEEE Transactions on Medical Imaging, vol. 7, No. 4 Dec. 1988 entitled Sprint II: A Second Generation Single Photon Ring Tomograph by W.L. Rogers, N.H. Clinthorne, L. Shao, P. Chiao, Y. Ding, J.A. Stamos, and K.F. Koral.

(List continued on next page.)

Primary Examiner—Constantine Hannaher
Assistant Examiner—Otilia Gabor
(74) Attorney, Agent, or Firm—Gifford, Krass, Groh, Sprinkle, Anderson & Citkowski, P.C.

(57) ABSTRACT

A single photon emission computed tomography system produces multiple tomographic images of the type representing a three-dimensional distribution of a photon-emitting radioisotope. The system has a base including a patient support for supporting a patient such that a portion of the patient is located in a field of view. A longitudinal axis is defined through the field of view. A generally arcuate detector assembly is adjacent the field of view. The detector assembly extends generally arcuately at least partially about the field of view between a pair of ends. The ends are spaced apart so as to define an entry opening to the field of view. The detector assembly includes a plurality of photon-responsive detectors arranged along the arcuate detector assembly, with each detector being operable to detect if a photon strikes the detector. A generally arcuate photon-blocking member is positioned between the field of view and the detectors. The blocking member has a plurality of aperture slots defined therethrough at intervals along the member for passage of photons aligned with the aperture slots. A line of response for each of the detectors is defined from each detector through the nearest of the aperture slots. A displacement actuator moves the photon-blocking member relative to the detectors such that the aperture slots are displaced relative to the detectors and the lines of response are swept across at least a portion of the field of view.

26 Claims, 14 Drawing Sheets

OTHER PUBLICATIONS

IEEE Transactions on Nuclear Science, vol. NS–26, No. 1, Feb. 1979 entitled Introducing Sprint: A Single Photon Ring System for Emission Tomography by J.J. Williams, W.P. Snapp, G.F. Knoll.

Performance Evaluation of Sprint, A Single Photon Ring Tomograph for Brain Imaging by W. Leslie Rogers, Neal H. Clinthorne, John Stamos, Kenneth F. Koral, Robert Mayans, Glenn F. Knoll, Jack Juni, John W. Keyes, Jr., and Beth A. Harkness.

IEEE Transactions on Medical Imaging, vol. MI–1, No. 1, Jul. 1982 entitled A Stationary Detector Single Photon Ring Tomograph for Brain Imaging by W.L. Rogers, N.H. Clinthorne, J. Stamos, K.F. Koral, R. Mayans, J.W. Keyes, Jr., J.J. Williams, W.P. Snapp, and G.F. Knoll.

IEEE Transactions on Nuclear Science, vol. 40, No. 4, Aug. 1993, entitled Ultra–High–Resolution Brain Spect Imaging: Simulation Results by M.M. Rogulski, H.B. Barber, H.H. Barrett, R.L. Shoemaker and J.M. Woolfenden, University of Arizona, Tucson, AZ 85724.

* cited by examiner

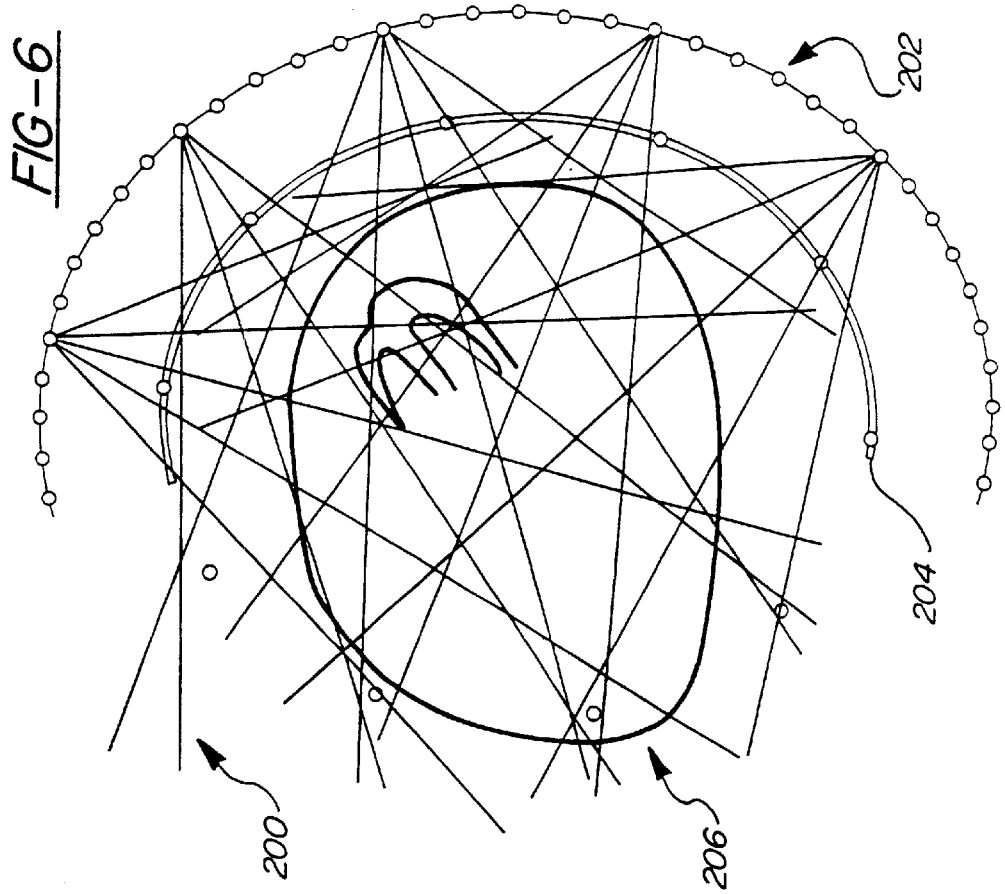
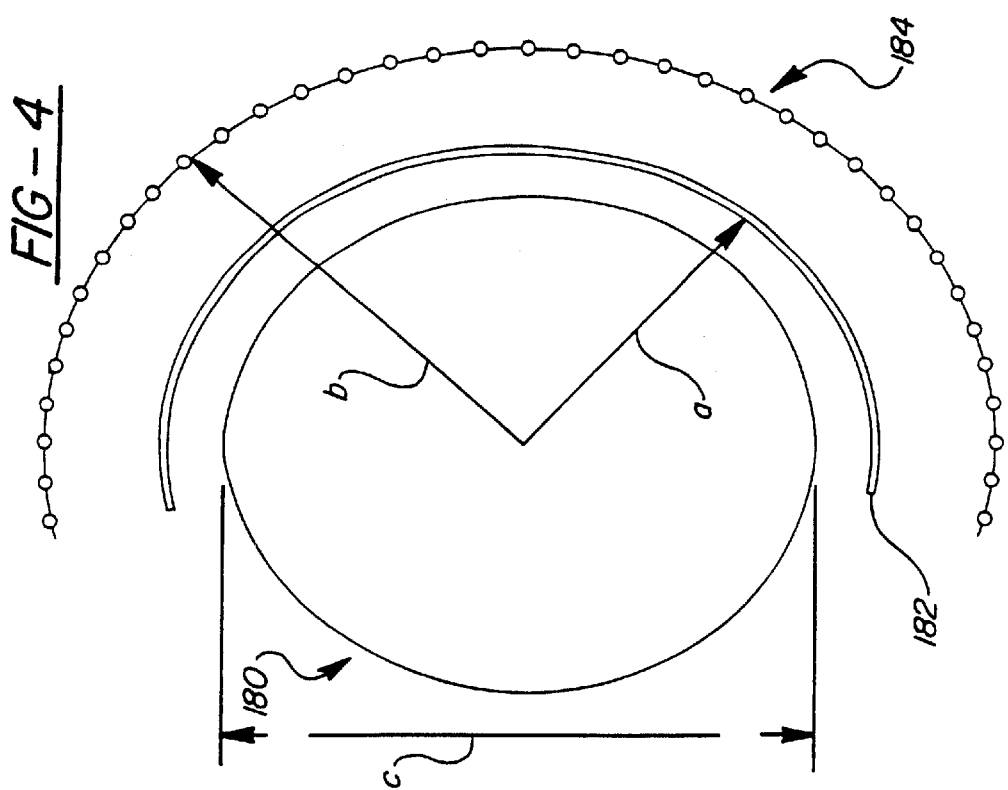

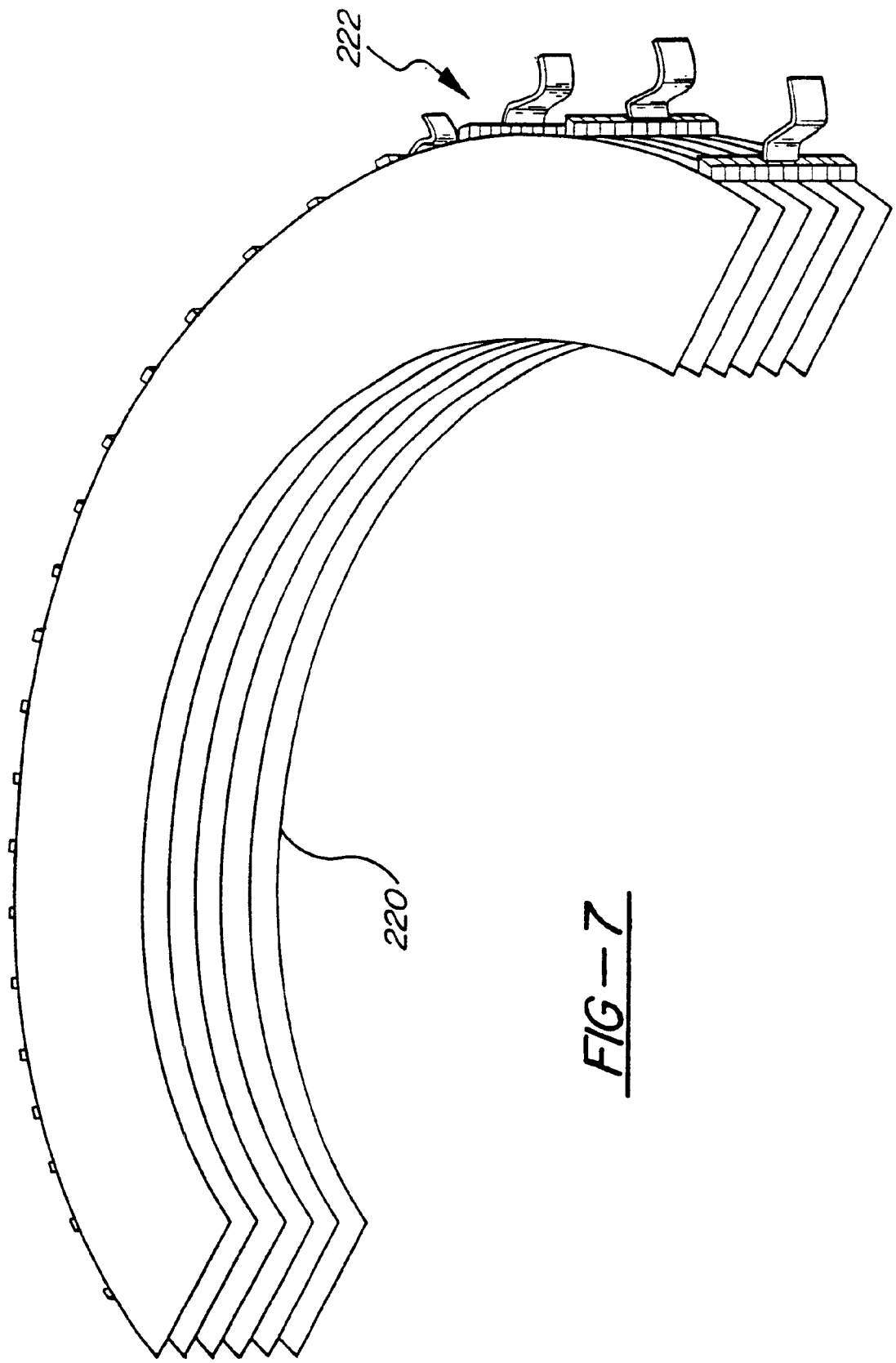

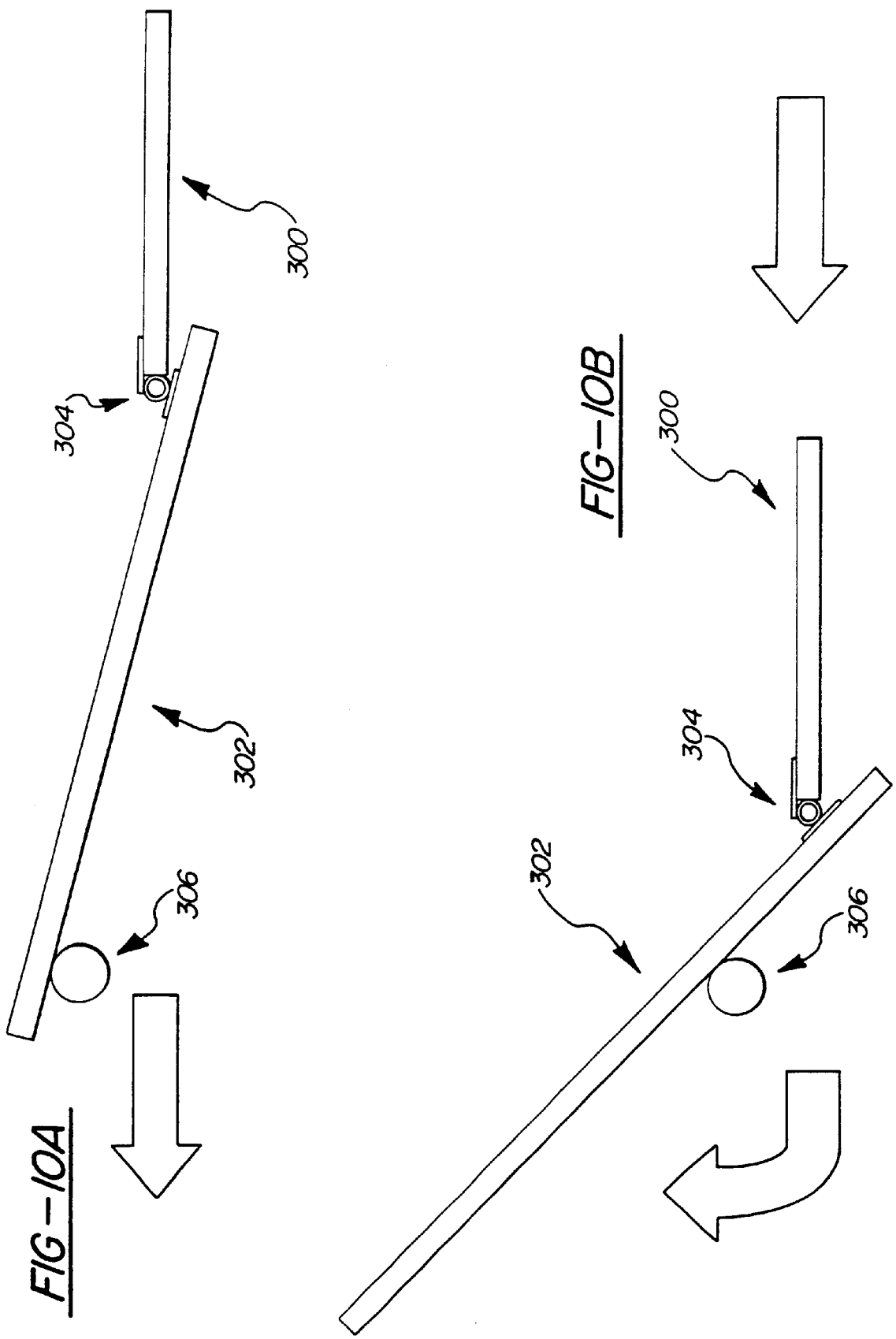

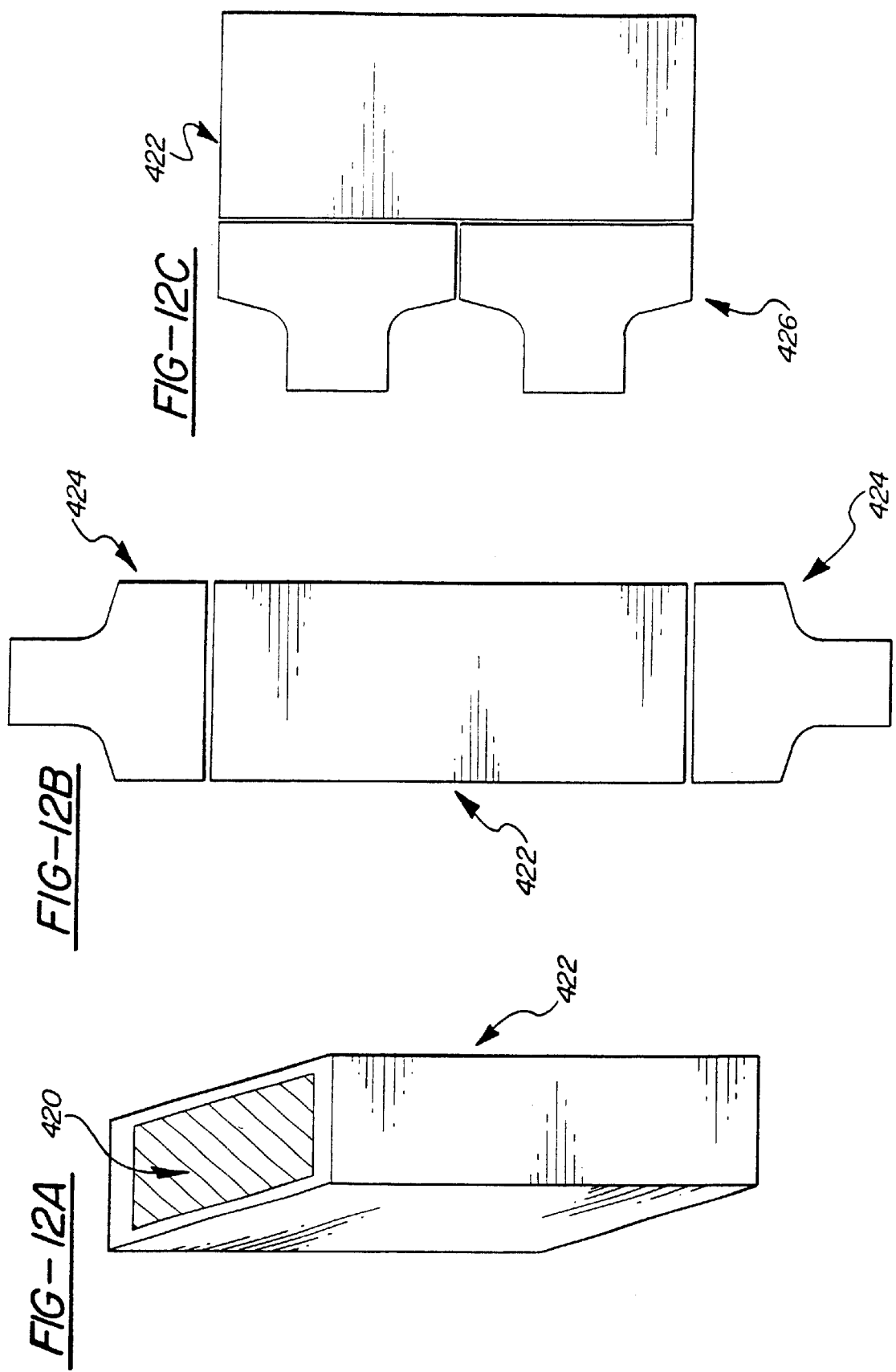

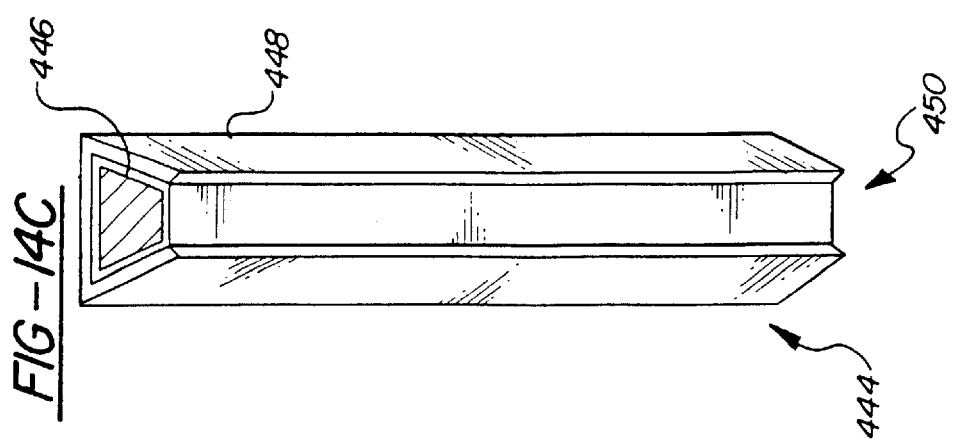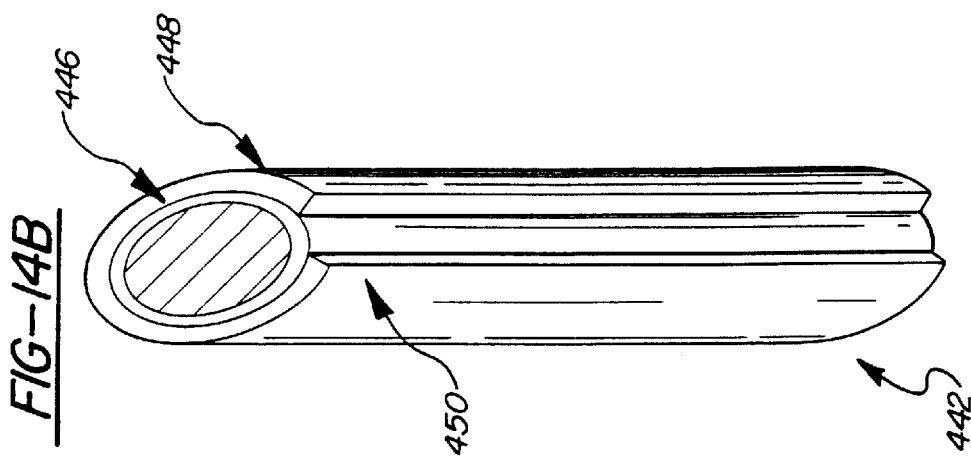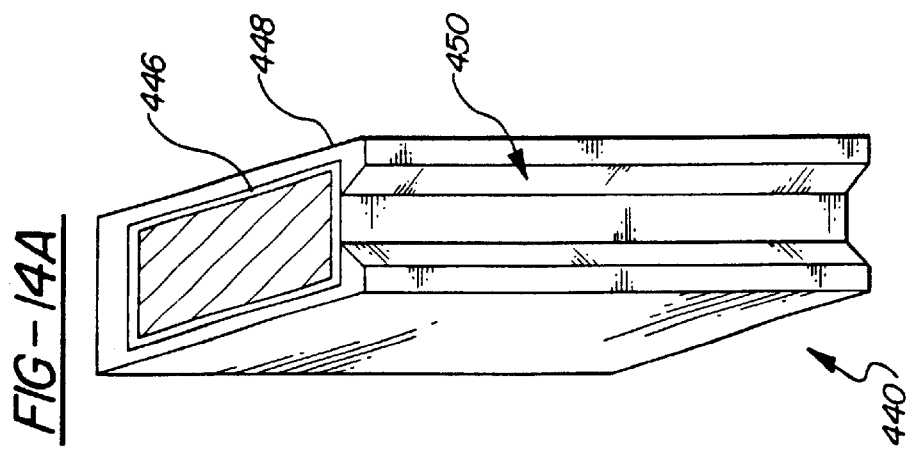

SINGLE PHOTON EMISSION COMPUTED TOMOGRAPHY SYSTEM

CROSS-REFERENCE TO RELATED APPLICATIONS

This application is a continuation of U.S. patent application Ser. No. 09/549,435 filed Apr. 14, 2000, which claims the benefit of U.S. Provisional Applications having Serial No. 60/129,239 filed Apr. 14, 1999 and Ser. No. 60/151,378 filed Aug. 30, 1999, all of which are incorporated herein in their entirety by reference.

BACKGROUND OF THE INVENTION

Medical radionuclide imaging (Nuclear Medicine) is a key component of modern medical practice. This methodology involves the administration, typically by injection, of tracer amounts of a radioactive substance, which subsequently localizes in the body in a manner dependent on the physiologic function of the organ system being studied. The radiotracer emissions, most commonly gamma photons, are imaged with a detector outside the body, creating a map of the radiotracer distribution within the body. When interpreted by an appropriately trained physician, these images provide information of great value in the clinical diagnosis and treatment of disease. Typical applications of this technology include detection of coronary artery disease (thallium scanning) and detection of cancerous involvement of bones (bone scanning). The overwhelming bulk of clinical radionuclide imaging is performed using gamma emitting radiotracers and detectors known as "gamma cameras".

Gamma cameras typically consist of a large scintillation crystal (e.g. sodium iodide) having the property of emitting light when struck by gamma photons. Affixed to the rear of this crystal are multiple photomultiplier tubes with associated circuitry to detect the light flashes and to locate their position within the scintillation crystal. In front of the crystal is a collimator, typically consisting of several millimeters of lead with multiple holes penetrating it. The collimator serves to absorb all incoming photons except those approaching the crystal generally from the appropriate direction. The crystal, photomultiplier tubes and associated circuitry are typically enclosed in a large lead case that serves to shield the detector from unwanted external radiation. The entire apparatus is mounted on a gantry with a motorized apparatus for positioning the detector near the patient.

A gamma camera provides a two-dimensional image of radiotracer distribution. However, the distribution of radiotracers within the body is typically three-dimensional. The technique of single photon emission tomography (SPECT) is used to create three-dimensional, tomographic images similar to a "radionuclide CT scan" by using computer processing to "reconstruct" the three-dimensional tracer distribution from a series of two-dimensional gamma camera images obtained from multiple angles around the patient. This is almost universally accomplished by mounting one or more gamma cameras to a motorized gantry and orbiting them around the patient. The data thus acquired is then processed to yield the three-dimensional images.

The three-dimensional SPECT images have been demonstrated to provide higher image contrast and to reduce apparent overlap of body structures. SPECT imaging is now considered to be the state-of-the-art in radionuclide imaging of the heart and now accounts for more than half of all cardiac nuclear imaging performed in the United States.

Despite its many advantages, SPECT imaging is not yet available to all patients who might benefit from it. Current SPECT instrumentation has a number of disadvantages which have impeded its wider implementation.

Current SPECT systems are bulky, typically requiring a large, dedicated room to house them. The collimating systems are relatively inefficient, blocking a high percentage of emitted radiation. Thus, most new clinical systems simultaneously utilize two or more gamma camera detectors mounted on a single gantry. Since each detector typically weighs several hundred pounds, the supporting gantry must be large and heavy. Most SPECT installations require specially constructed rooms with added floor reinforcement. Since accurate image reconstruction requires precise detector placement, SPECT systems require heavy positioning systems consisting of motors and gearing capable of moving and positioning hundreds of pounds of apparatus to a precision of approximately a millimeter. These systems are necessarily large, heavy and expensive.

Although there is great medical need to image patients in a variety of settings, including doctors' offices, emergency rooms and intensive care units, 0the great size and bulk of current SPECT systems has required them to be in a fixed location, typically a hospital Radiology or Nuclear Medicine department. There are significant medical and patient convenience advantages to having cardiac SPECT imaging performed in the immediate presence of the attending Cardiologist. Many studies have shown that the cost of care delivered in an outpatient office setting is less than that of a hospital setting. Despite these compelling factors, the size and cost constraints of current systems have greatly limited their penetration into the community and have particularly limited their availability in physicians' offices. In addition, the large space requirements of current systems have imposed significant costs on hospitals providing SPECT services.

Current SPECT systems have additional limitations. As the gamma cameras orbit around the patient, large multi-conductor cables are required to carry power and data to and from each detector. These cables are repeatedly flexed during system operation and are a frequent cause of equipment breakdown.

The large and heavy nature of existing systems has dictated a mechanical gantry design that is highly stable, yet cost effective. This has resulted in systems in which the patient must lie in a supine (flat on the back) position on a narrow platform that extends into a vertically oriented gantry. In order to permit the detectors to be as close as possible to the chest and to enable the large, moving detectors to safely pass around the patient, current systems require the patient to maintain one or both arms in an uncomfortable position held over the head. This is painful for most patients and impossible for some. In addition, the supine position is uncomfortable for many patients, particularly for those with back problems. Many patients feel claustrophobic when inside the equipment. The narrow platform required to permit camera rotation around the patient is uncomfortable for large individuals and is often perceived as insecure or precarious by those undergoing scans. Also, the fact that the patient is partially enclosed by the equipment during imaging may serve to limit physician or nursing access to critically ill patients.

SUMMARY OF THE INVENTION

The invention described herein is a system for performing single photon emission computed tomographic imaging (SPECT) that is especially suitable for cardiac imaging. Embodiments that are optimized for breast and for brain imaging are also described. The system has a base including a patient support for supporting a patient such that a portion of the patient is located in a field of view. A longitudinal axis is defined through the field of view. A detector module is adjacent the field of view and includes a photon-responsive detector. The detector is an elongated strip or bar with a central axis that is generally parallel to the longitudinal axis. The detector is operable to detect if a photon strikes the detector. The detector also includes means to determine the position along the length of the strip where a photon is detected. A photon-blocking member is positioned between the field of view and the detector. The blocking member has an aperture slot for passage of photons aligned with the aperture slot. The slot is generally parallel to the longitudinal axis. A line of response is defined from the detector through the aperture. A displacement device moves either the detector module or the photon-blocking member relative to the other so that the aperture is displaced relative to the detector and the line of response is swept across at least a portion of the field of view.

In one embodiment of the present invention, the single photon emission computed tomography system has a base, including a patient support, for supporting a patient such that a portion of the patient is located in a field of view. A longitudinal axis is defined through the field of view. A generally arcuate detector assembly is adjacent to the field of view. The detector assembly extends generally arcuately at least partially about the field of view between a first end and second end. The first and second ends are spaced apart so as to define an entry opening to the field of view. The detector assembly includes a plurality of photon-responsive detectors arranged along the arcuate detector assembly, with each detector being operable to detect if a photon strikes the detector. A generally arcuate photon-blocking member is disposed between the field of the view and the detectors. The blocking member has a plurality of aperture slots defined therethrough at intervals along the member. The apertures allow passage of photons aligned with the aperture slots. A line of response for each of the detectors is defined from each detector through the nearest of the aperture slots. A displacement actuator is operable to move the photon-blocking member relative to the detector such that the aperture slots are displaced relative to the detectors and the lines of response are swept across at least a portion of the field of view. Alternatively, the displacement actuator may be operable to move the detectors relative to the photon-blocking member.

Multiple unique configurations of detector modules are also described. The system may be provided with an adjustable chair permitting comfortable patient positioning and adjustment within the imaging system.

BRIEF DESCRIPTION OF THE DRAWINGS

FIG. 1b is an additional perspective view of the embodiment of FIG. 1a;

FIG. 4 is a diagrammatic top view showing the relative positions of the slotted aperture arc, the arc of detectors and the patient field-of-view;

FIG. 6 is a diagrammatic top view showing how lines of response of the individual detectors provide multiple angular projections through the body;

FIG. 7 is a perspective view of a cross-plane (longitudinal) collimation assembly showing its relationship to the detector modules;

FIG. 10a is a cross sectional top view of one embodiment of a moveable aperture arc extension vane;

FIG. 10b is a view similar to FIG. 10a with the vane shown at a different position;

FIG. 12a is a perspective view of another embodiment of a detector module using a rectangular bar-shaped piece of scintillation material;

FIG. 12b is a side elevational view of the module of FIG. 12a with photo detectors at the top and bottom;

FIG. 12c is a view similar to FIG. 12b but with the photo detectors positioned at the rear face of the scintillation material;

FIG. 14a is a perspective view of a masked detector configuration based on a rectangular shaped piece of scintillation material;

FIG. 14b is a perspective view of a masked detector configuration based on a cylindrical shaped piece of scintillation material;

FIG. 14c is a perspective view of a masked detector configuration based on a piece of scintillation material with a trapezoidal cross section;

DETAILED DESCRIPTION OF THE INVENTION

Throughout this description, the preferred embodiment and examples shown should be considered as exemplars rather than as limitations on the present invention.

The present invention comprises a system for performing single photon emission computed tomography (SPECT). The system includes a radiation detector assembly consisting of a multiplicity of radiation detector modules preferably positioned around an arc, typically over 180°–360°. In-plane (axial) collimation is provided by a movable arc or ring extending over an angular range similar to that of the radiation detector assembly (typically 180°–360°). Cross-plane (longitudinal) collimation is provided by a plurality of vanes or sheets of photon-attenuating material held in a stationary position and oriented parallel to the transaxial plane (perpendicular to the longitudinal axis). Optionally, these vanes may be separated by sheets of a radiolucent spacer material such as Styrofoam® or other plastic. Some embodiments of the present invention also include a patient chair or support structure.

Figure 1B:
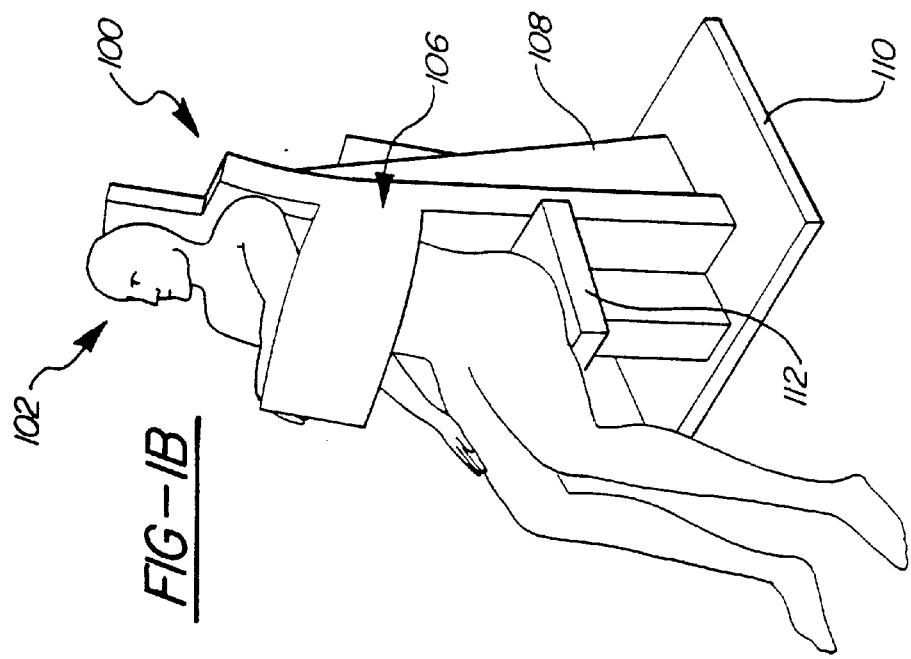
Figure 1A:
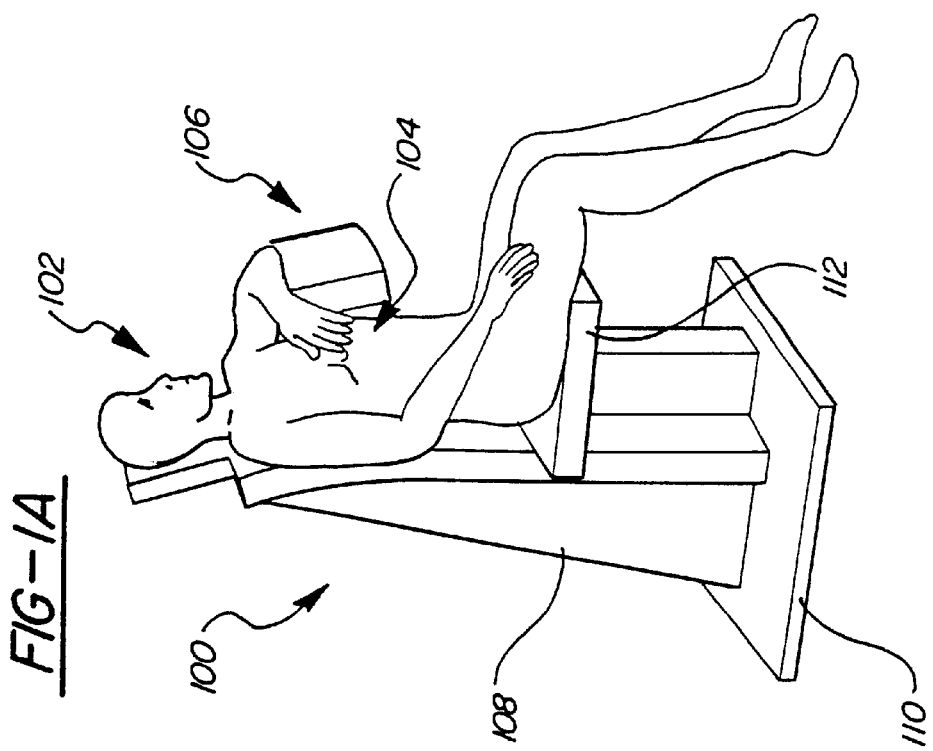
FIG. 1a is a perspective view of a preferred embodiment of the present invention optimized for cardiac SPECT, showing the overall configuration of the system and the positioning of the patient.

FIGS. 1a and 1b illustrate a preferred embodiment of the present invention optimized for cardiac SPECT, showing the overall configuration of the system 100 and the positioning of the patient 102. The opening 104 for patient entry and egress is shown. The imaging section 106 of the system extends as an arc over the right side of the patient's chest. The imaging section consists of a lead shielded housing with internal components as described below. The imaging section is supported in a stand 108 affixed to a base 110. Together, the rear portion of the imaging section and the stand form the "back" of the patient support. The patient is seated upon an adjustable seat 112. The vertical height of this seat may be adjusted so as to position the patient's heart within the appropriate portion of the imaging device. Such adjustment may be performed by means of electrical motors, hydraulic devices or other means. The seat is optionally adjustable so as to swivel horizontally, thus easing patient entry and egress from the seated position. The stand and base may also include or support the electronics necessary for processing scans, as well as any necessary controls or displays.

As shown, unlike in the prior art systems, the patient is seated generally upright so that their torso is generally vertical. The lighter weight, simpler design, and reduced bulk of the present system cooperate to allow this positioning. For definitional purposes, the area surrounded by the imaging section 106 will be referred to as a field of view. Also for definitional purposes, it may be said that a longitudinal axis, generally aligned with the longitudinal axis of the patient's torso, extends through the field of view. It may be said that the longitudinal axis is generally vertical to distinguish the positioning of the present system from the typical systems where the patient is forced into a horizontal system. In actuality, the generally vertical longitudinal axis may be reclined somewhat, as shown, to increase patient comfort.

Figure 2:
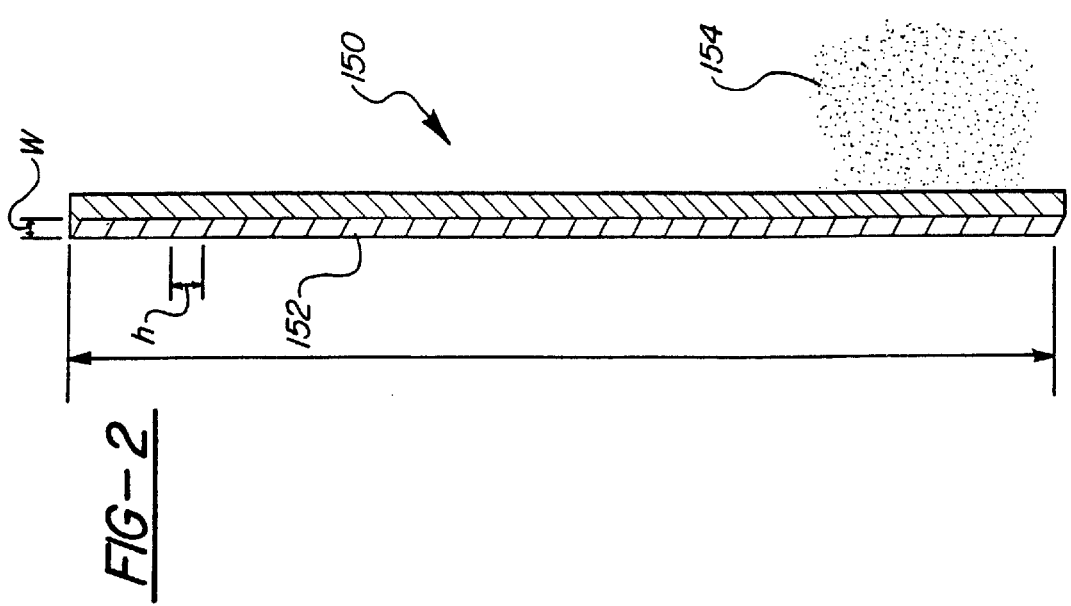
FIG. 2 is a perspective view of one embodiment of an individual detector module for detecting photons during SPECT imaging.

FIG. 2 shows one embodiment of an individual detector module 150. Multiple (typically 64) individual modules are arranged in an arc surrounding the patient. The arc may extend over a range of approximately 180°–360°. For cardiac SPECT, a preferred embodiment is approximately 180°. The embodiment shown is a solid-state detector module sized for cardiac imaging. Other detector module embodiments are discussed below. As shown, the detector module 152 is an elongated strip. Rectangular regions on the face of detector indicate an array of individual solid-state detector elements 152, each comprising one pixel for data acquisition. In this embodiment, the array of detector elements is one-dimensional, i.e. 1×N, although two-dimensional arrays may also be employed. Multiconductor ribbon cable 154 carries electrical signals from the detector elements to the electronics that process the signals. Alternatively, some of the processing circuitry may be integral with or packaged by the detector elements. Each detector element 152 is operable to detect if a photon strikes it. Therefore, the overall detector 150 is operable to detect if a photon strikes and is also operable to determine where along its length the photon struck. Each detector element includes some semiconductor material, such as cadmium-zinc-telluride, with an electrode applied to opposing surfaces. An electrical potential is applied across the electrodes. As will be clear to those of skill in the art, when a photon passes through the front electrode and interacts with the semiconductor material, a small current travels between the electrodes. This current is measured to sense the impact of photons.

In some embodiments, the individual detector elements 152 have a width, w, of approximately 4 mm and a height, h, of 6 mm. Previous attempts to provide solid state detectors have focused on providing much smaller detector elements. However, because of the difficulty in reliably producing the solid state detectors, smaller detector elements frequently have flaws that make the entire element unusable. The larger detector elements preferably used in the present invention overcome this difficulty because it is much less likely for a flaw to make the larger element completely unusable. Instead, the sensitivity of an element with a flaw may be somewhat reduced. This reduction in sensitivity may be compensated for by the electronics that receive and process signals from the detectors and/or by software processing of the signals.

Figure 3:
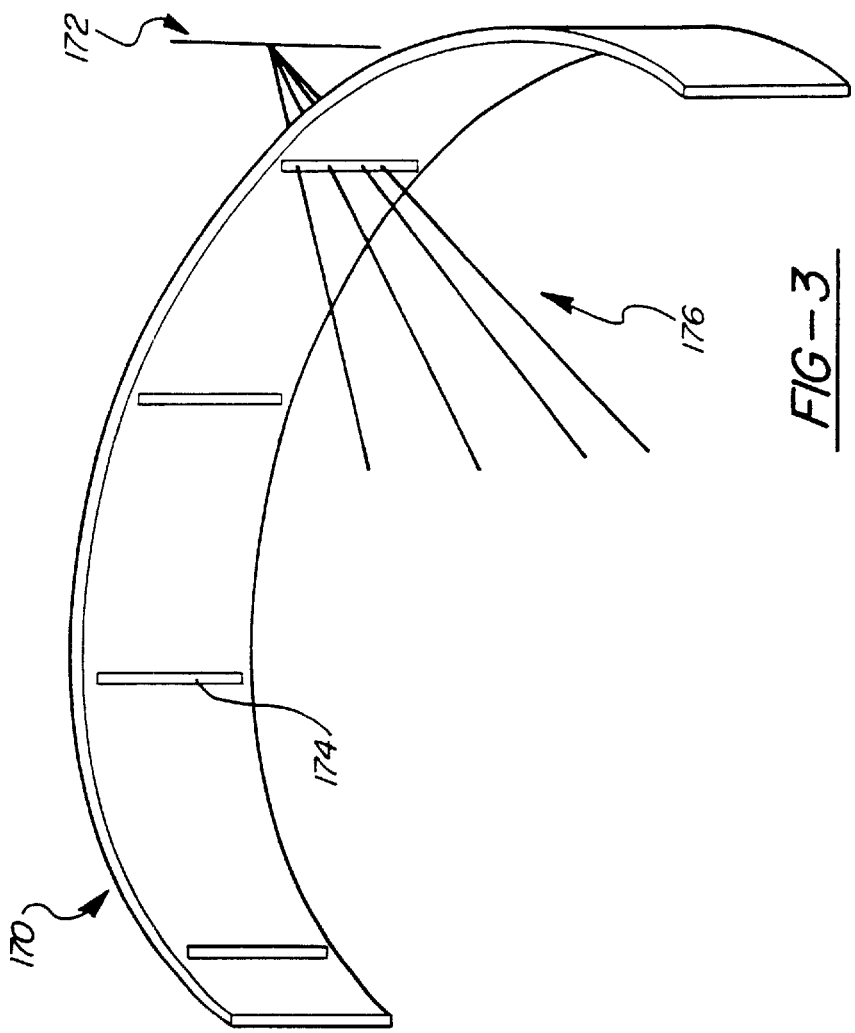
FIG. 3 is a perspective view of an aperture arc for an embodiment of the present invention that is optimized for cardiac SPECT, with a single radiation detection module shown behind the arc to demonstrate relative positioning.

FIG. 3 shows the aperture arc 170 for an embodiment optimized for cardiac SPECT. A single radiation detector module 172 is shown behind the arc to demonstrate relative positioning. As shown, the detector module is generally parallel to the longitudinal axis. The arc 170 serves as a photon-blocking member and may be made of lead or a similar high attenuation material. The arc 170 is of sufficient height to cover the radiation detection modules 172 situated behind it. The arc is of sufficient thickness (typically approximately 3 mm) so as to effect essentially complete absorption of photons emitted by the patient. The arc is penetrated by a series of vertical aperture slots 174 which permit photons 176 aligned with the aperture slot to pass from the patient through the slot to reach the detector modules. The slots are preferably generally parallel to the longitudinal axis of the patient.

FIG. 4 diagrams (from above) the relative positions of the patient field-of-view area 180, the aperture arc 182 and the detector modules 184. It may be seen that the set of detector modules and the aperture arc are situated concentrically around the patient. A typical embodiment for cardiac imaging will include approximately 64 radiation detector modules 184, each consisting of an array of individual elements or pixels. In one embodiment, the aperture arc 182 is positioned at a radius, a, of approximately 30 cm and the detector modules 184 are positioned at a radius, b, of approximately 40 cm. A patient field-of-view area with a diameter, c, of approximately 50 cm fits easily within the arc 182.

Displacement means is provided for moving the aperture arc 182 relative to the detectors 184. As will be clear to those of skill in the art, many different approaches may be used to move the aperture arc. For example, the aperture arc 182 may connected by a worm gear or other arrangement to a motor such that it can be rotated through a limited angle about the longitudinal patient axis. As will be clear to those of skill in the art, the arc may remain stationary with only the detectors moving. However, this approach is generally more complicated and costly. For purposes of processing the information from the scan, means are also provided for accurately determining the position of the arc. As will be clear to those of skill in the art, many approaches to providing this means are available, including optical encoders and mechanical sensors. The sensing means may also be used for feedback control of the displacement means.

Figure 5C:
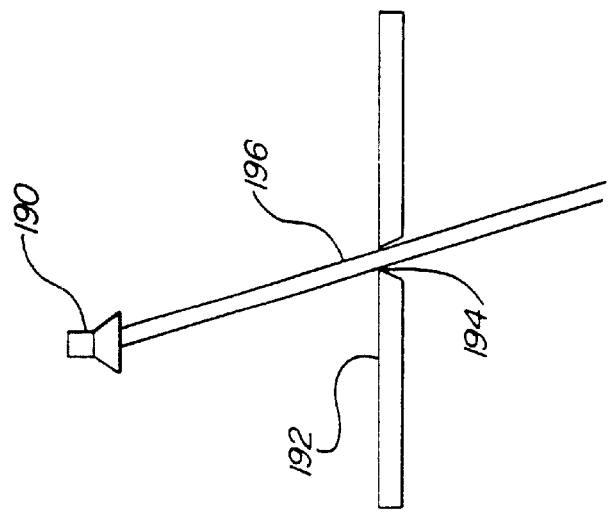
FIG. 5c is a view similar to FIGS. 5a and 5b but with the aperture arc at a third position.
Figure 5B:
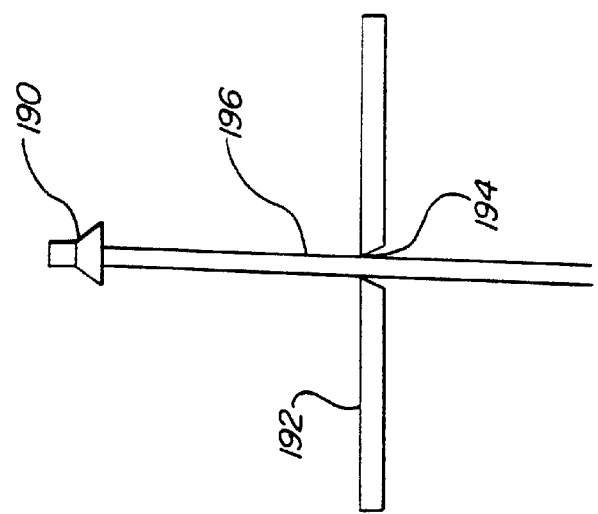
FIG. 5b is a view similar to FIG. 5a but with the aperture arc at a second position.
Figure 5A:
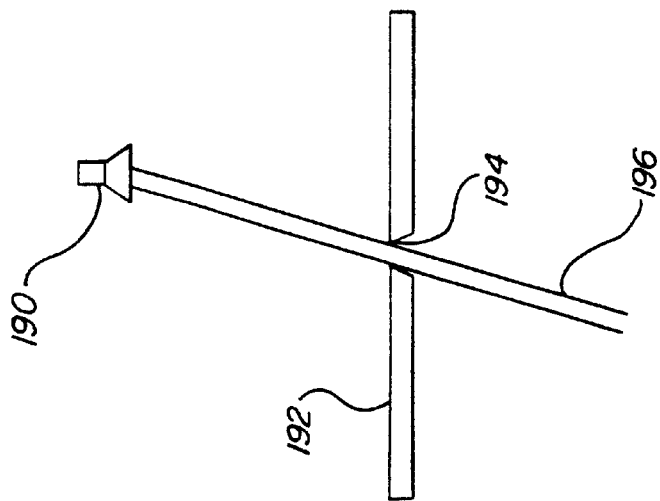
FIG. 5a is a top schematic view of a single detector module and a small section of the aperture arc at a first rotational position of the aperture arc.

FIGS. 5a–c show overhead views of a single detector 190 and a small section 192 of the aperture arc. The Figures illustrate the relative position of the arc 192 and the detector 190 at three different rotational positions of the aperture arc 192. At each position, the position of the aperture slot 194 restricts the line of response of the detector to a particular path 196 as shown. It can be seen that, as the aperture slot 194 moves in front of the detector 190, the line of sight of the detector fans across the patient, generating a multiplicity of lines of response or projections.

Since, as diagrammed in FIG. 4, there are a multiplicity of detector modules 184 and, as shown in FIG. 3, a multiplicity of aperture slots 174, a multiplicity of detector lines of response are formed at each rotational position of the aperture arc. FIG. 6 illustrates a small subset of the lines of response 200 obtained from a few of the detectors 202 as the aperture arc 204 is rotated. The aperture slots themselves are not shown on this figure for simplicity. A diagrammatic "slice" 206 through the patient's chest is shown, indicating that a full set of projections of the heart, sufficient for tomographic reconstruction, is obtained in this manner.

All detector "look through" one slot at all times. Slot spacing is determined such that each detector is illuminated by only one slot at a time. Overall photon detection efficiency is proportional to the number of slots in the aperture arcs. The maximum number of slots permissible, $n_{slots}$, is therefore a function of the angle $\Phi_{arc}$ spanned by the aperture arc and the detector arc and the minimum length of arc $\theta_A$ on the aperture arc such that a given detector will only see the patient field-of-view through one slot at a time:

$$n_{slots} = \frac{\pi \cdot \frac{\phi_{arc}}{2\pi}}{\frac{\theta_A}{2}} = \frac{\pi \cdot \frac{\phi_{arc}}{2\pi}}{\sin^{-1}\left(\frac{R_O}{R_A}\right) - \sin^{-1}\left(\frac{R_O}{R_D}\right)}$$

Where $R_O$ is the radius of the patient, $R_A$ is the radius of the aperture arc and $R_D$ is the radius of the detector arc. The aperture arc need only be rotated by the interval between slots, $\Phi_{arc}/n_{slots}$, to provide a full set of angular projections.

Taken together, the aperture arc and the set of detectors would provide projection data collimated within the transaxial plane, but not collimated longitudinally. For this reason, the invention preferably provides a set of longitudinal or cross-plane collimators as shown in FIG. 7. The longitudinal collimators consist of a stack-like series of arc-shaped vanes 220 arranged as shown and located concentrically to the arc arrangement of detectors 222 as shown. The aperture arc is omitted from this figure, but is located concentrically to the longitudinal collimator vanes. The vanes are preferably mutually parallel and generally perpendicular to the longitudinal axis of the patient. The vanes are constructed of a small thickness (typically less than 1 mm) of lead or similar attenuating material and may be separated by spacers of radiolucent plastic foam or similar material (not shown). The number, size, and thickness of the vanes may be varied depending on the application.

Figure 8:
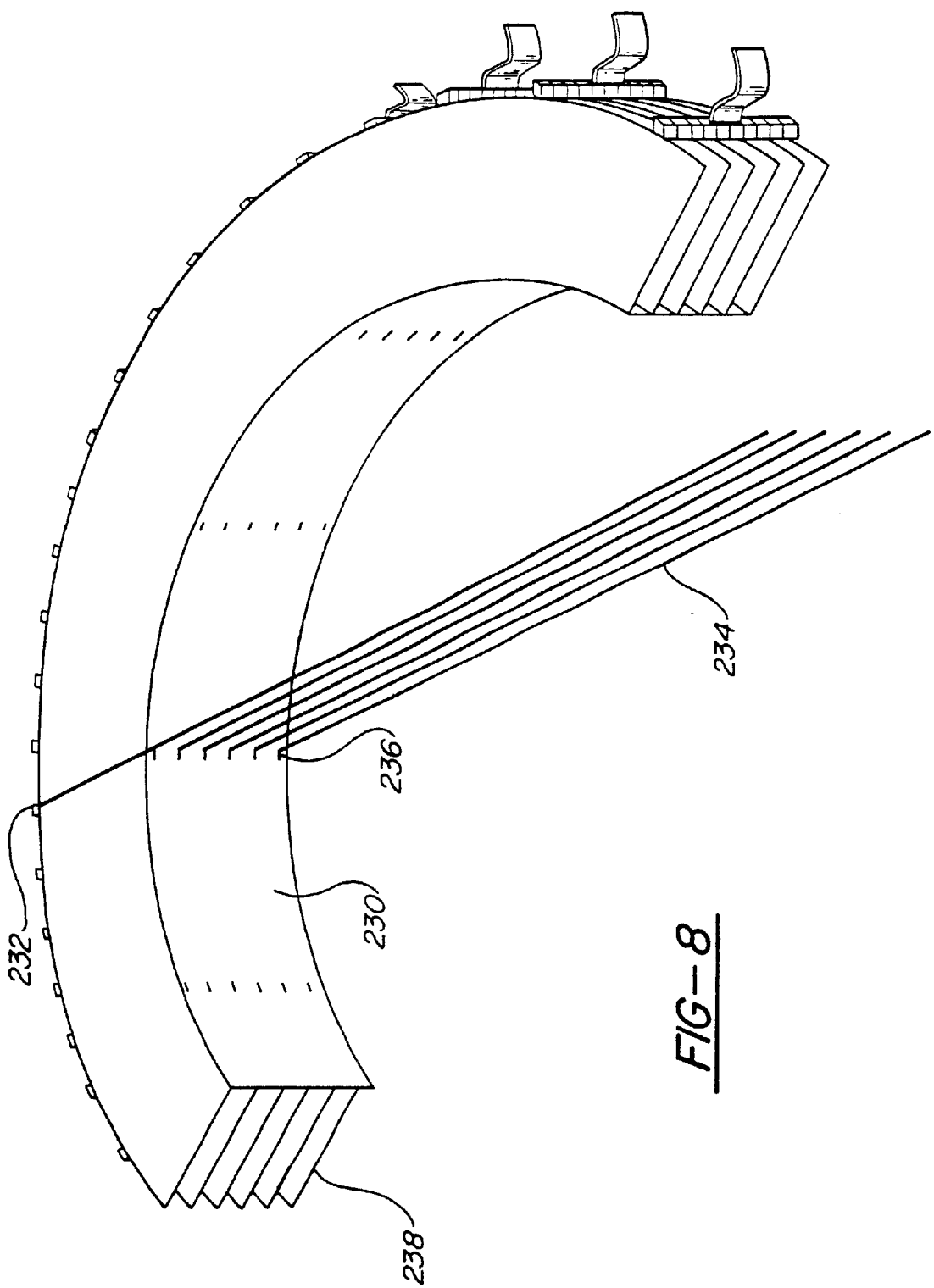
FIG. 8 is a view similar to FIG. 7 but including the aperture arc and showing the lines of response from one detector module.

FIG. 8 is similar to FIG. 7 but with the addition of the aperture arc 230. It may be seen that each individual detector element (pixel) of each detector 232 has a unique line-of-response 234 directed into the patient field-of-view by the combined collimating effects of the aperture arc slots 236 and the longitudinal collimating vanes 238.

The in-plane resolution of this system is determined by the radii of the detector and aperture arcs, $R_D$ and $R_A$, the distance, Dist, of the object from the aperture arc, and the widths of the slots and the detector elements, $W_{slot}$ and $W_{det}$ respectively:

$$\text{resolution} \approx W_{slot} + \frac{Dist \times (W_{slot} + W_{det})}{(R_D - R_A)}$$

Figure 9:
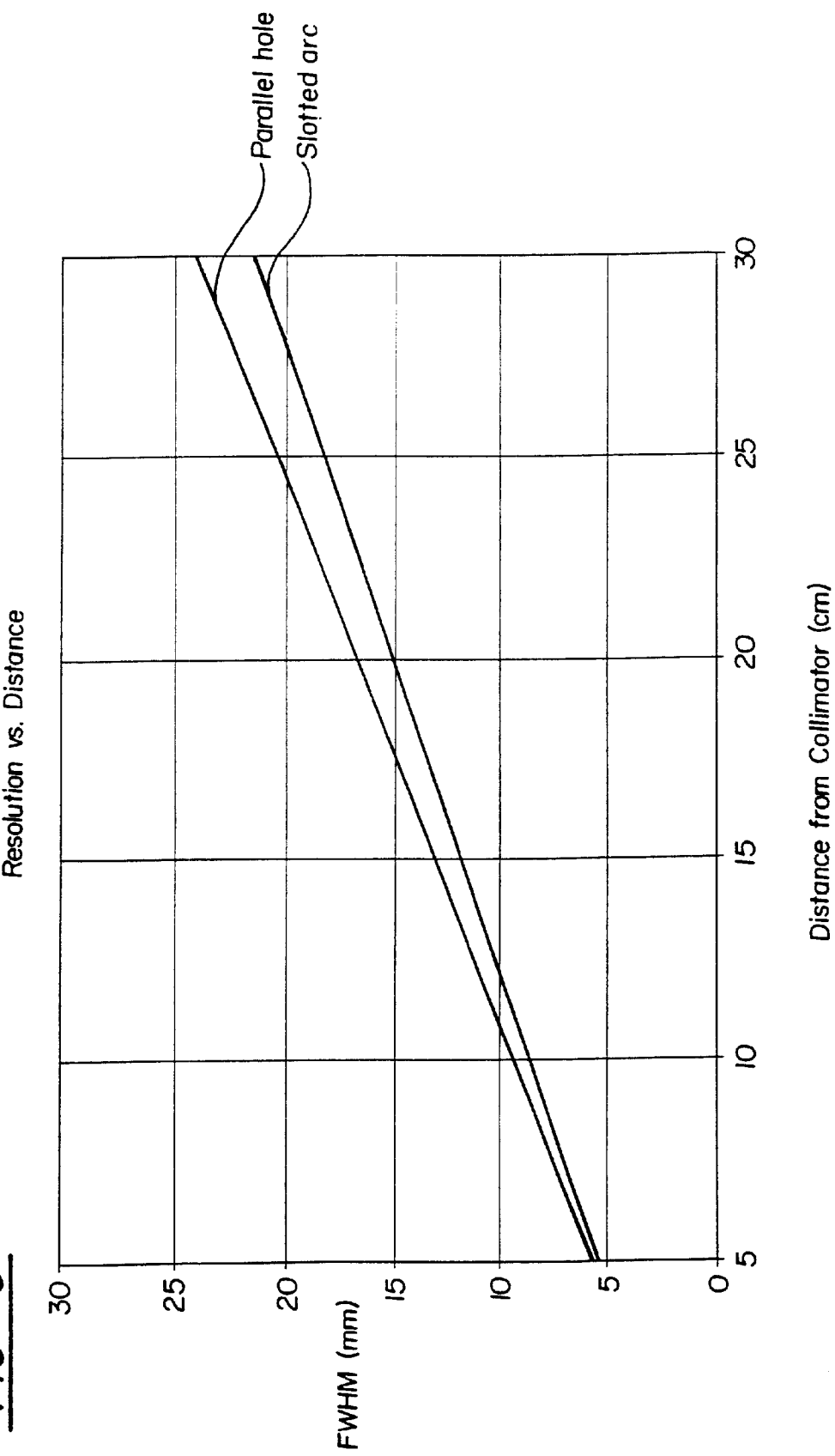
FIG. 9 is a plot showing the in-plane spatial resolution at different depths using the present invention versus a traditional "high resolution" parallel-hole collimator.

FIG. 9 plots the resolution at different depths of the present invention versus a traditional parallel-hole collimator. The slotted arc system is assumed to have a slot width of 2.4 mm, a detector width of 4 mm and other parameters as discussed with respect to FIG. 4. The parallel-hole collimator for which data is plotted has a hole diameter of 2.2 mm and a collimator thickness of 3 cm.

The detection efficiency of the slotted aperture system is proportional to the detector solid angle, $\Omega$, for a point source at the center of the field-of-view and may be calculated based on Rogers (IEEE TIMI, vol. MI-1, pp. 63–68, 1982) as:

$$\Omega = n_{slots} \frac{1}{R_D^2} \left[ \sqrt{r_{obj}^2 - r_D^2} \cdot \frac{1}{R_A} \sqrt{[r_{obj}(R_D - R_A)]^2 - [R_A r_D]^2} \right] f p_{det}$$

where $r_{obj}$ and $r_D$ are the full-width-half-maximum object and detector resolution respectively, $p_{det}$ is the detector packing fraction and f is the fraction of frontal area closed by the longitudinal collimating vanes. In the configuration of this invention, f=vane thickness/vane separation.

As the aperture arc moves to differing positions relative to the detectors, the apparent width of the aperture slots will vary as a function of the sine of the angle between the slot and the detector. Since the apparent width of the detector as viewed from the slot also changes according to a similar function, the overall detection efficiency will vary as a function of the square of the sine of the detector-slot angle. The exact function will depend on the photon cross-section of the detector element (a function of detector thickness) and on the photon cross-section of the slot aperture. This variation of detector sensitivity with slot position is easily mapped for a given detector and may be corrected for in software in a manner similar to the detector uniformity corrections routinely performed in traditional gamma cameras.

It is to be noted that imaging systems constructed according to the methods of this disclosure are relatively insensitive to the structured image artifacts seen in rotating gamma camera SPECT systems when non-uniformities of detector sensitivity exist. In the systems described here, the reduced count sensitivity of an relatively insensitive pixel is spread across the entire image plane, rather than appearing as the structured "ring" or "arc" artifacts seen in traditional systems.

As shown in FIGS. 1 and 4, for an embodiment optimized for cardiac imaging, the use of an arc shaped imaging apparatus allows the patient to easily enter and leave the imaging system. As the aperture arc rotates however, it will extend slightly into the open area of the arc. The invention therefore optionally provides for pivoted extension vanes to be located at one or both ends of the aperture arc, as shown in FIG. 10. This figure shows one end of the aperture arc 300 that includes an extension vane 302 extending its length.

FIG. 10a shows the aperture arc 300 and vane 302 at one extreme of the arc's movement and FIG. 10b shows them at the other extreme. Extension vane 302 is movably attached to the aperture arc by hinge 304. Pivot rod 306 is located in the path of the vane such that, as the extension vane is pushed against it by the movement of the aperture arc, the extension vane is caused to pivot away from the patient as shown in FIG. 10b. This minimizes the extension of the arc or vane into the opening while maintaining shielding of the detectors from unwanted external radiation.

Although FIG. 2 described a one-dimensional, linear array of solid-state detector elements, two-dimensional arrays are also provided in this invention. Such arrays may be provided as integral units or may be approximated by placing two or more one-dimensional arrays in close proximity. The overall sensitivity of the imaging system is linearly proportional to the detector surface area available.

Figure 11:
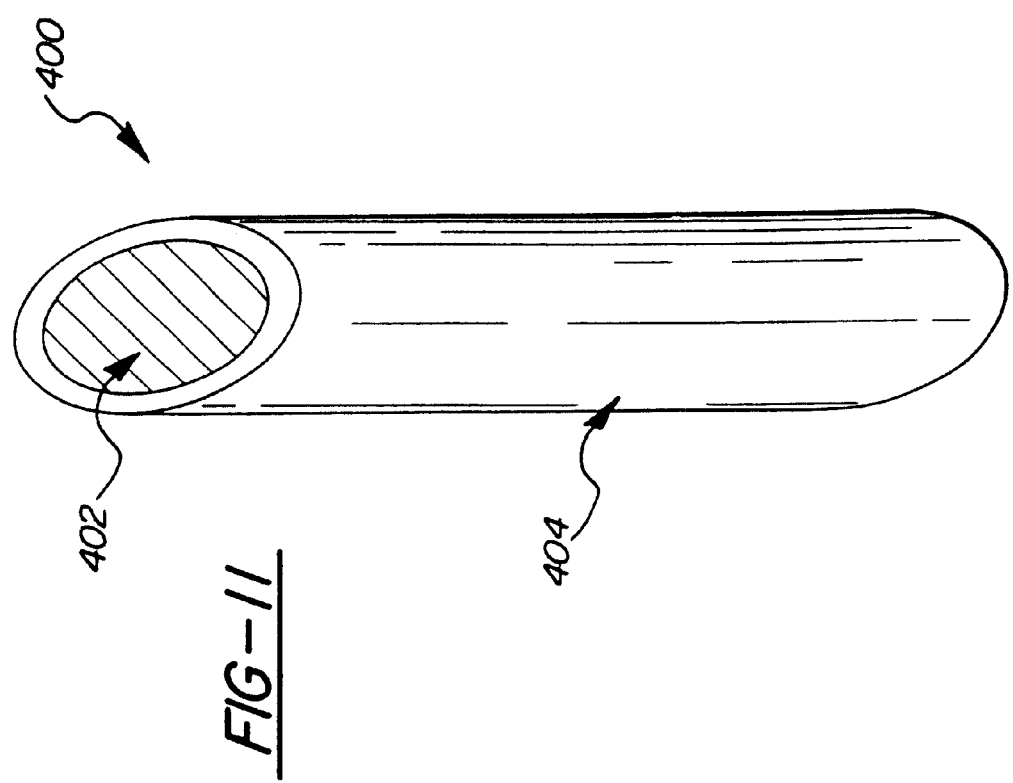
FIG. 11 is a perspective view of a portion of one embodiment of a scintillator-based cylindrical detector module.

This invention also provides for radiation detectors constructed from scintillation materials such as sodium iodide or cesium iodide with associated photomultiplier tubes or other photo-detectors such as solid state photodiodes. FIG. 11 shows one embodiment of a scintillation-based detector module 400. This embodiment includes a cylindrical crystal 402 of scintillation material clad in a radiolucent, light-reflective covering 404 such as aluminum. The covering 404 is open at both ends of the cylinder. Affixed to each end, via optical coupling material, is a light detector such as a photomultiplier tube, photodiode, or other photo-detector (not shown). The position of scintillation events occurring within the scintillation material is determined by the ratio of outputs of the two photo-detectors, thus providing longitudinal position sensing within the detector. This embodiment is extremely inexpensive to produce, but has the disadvantage of a variable photon detection efficiency across its horizontal dimension caused by the varying scintillator thickness over its circular cross-section. This causes a deviation of the detector's response function from a pure rect function, thus slightly degrading spatial resolution.

FIGS. 12a–c show more efficient embodiments of a scintillator-based detector, consisting of a rectangular bar 420 of scintillator material clad in a radiolucent, light-reflective material 422 such as aluminum. In FIG. 12b, the cladding is open at the top and bottom so as to permit placement of photo detectors 424. In the alternative embodiment shown in FIG. 12c, the cladding is open at the rear of the module so that two or more photo-detectors 426 can be affixed. In either case, the photo-detectors are considered to be adjacent the ends of the scintillation material so that they can locate the position of a scintillation event.

Figure 13:
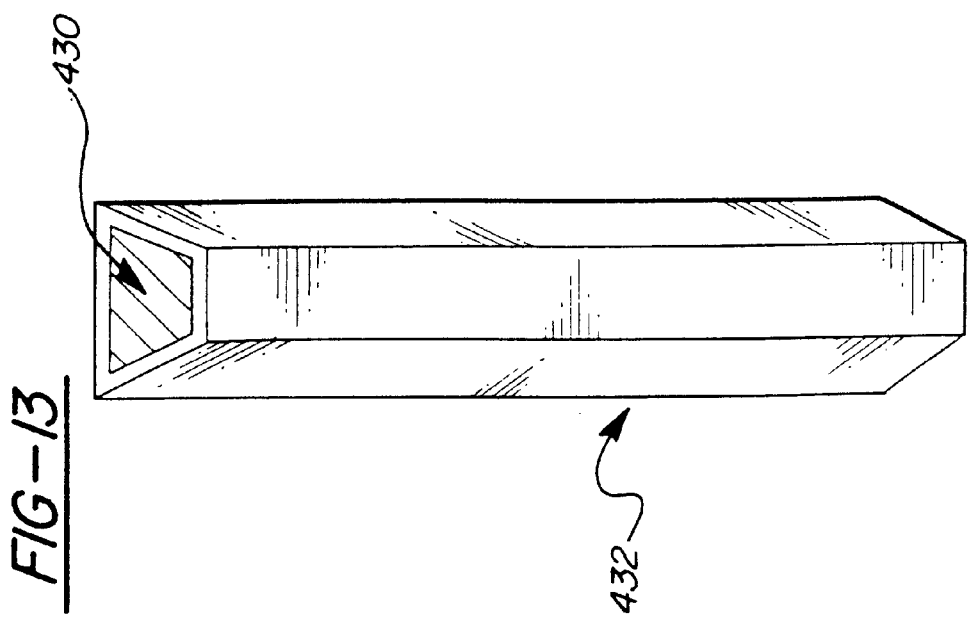
FIG. 13 is a perspective view of a detector module with a block of scintillation material with a trapezoidal cross section.

FIG. 13 shows a piece of scintillator material 430 with a trapezoidal cross section clad in reflecting material 432 as similar to the previous Figures. As with the embodiments of FIGS. 12a–c, the photo-detectors may be affixed on either the top and bottom of the module or at the rear face. The embodiment with the trapezoidal cross section has the advantage of presenting a more uniform cross-section to incoming radiation, but is more costly to manufacture. That is, radiation coming at an angle to the front face still encounters the full depth of the scintillator material.

Axial resolution of the tomography system is directly dependent on detector width, as described above. Specifically, narrower detectors increase the axial resolution of the system. As detector width narrows, however, photon detection efficiency drops because photons striking the front face of the narrow detector may scatter out of the detector material before they have deposited all their energy. According to the present invention, the efficiency of a high resolution elongated strip of scintillation material may be improved by masking a portion of its front face. FIG. 14a shows a detector configuration 440 based on a rectangular piece of scintillation material. FIG. 14b shows a detector configuration 442 based on a cylindrical piece of scintillation material. FIG. 14c shows a detector configuration 44 based on a piece of scintillation material with a trapezoidal cross section. In each of these embodiments, in addition to the reflective cladding 446, the scintillator is clad in an additional masking layer 448 of lead, tungsten or similar high-attenuation material. This outer masking or shielding layer is configured to have a narrow vertical opening 450 of the dimensions desired for the detector cross-section. Once photons have passed through the opening and struck the scintillator, further scattering is more likely to occur within the larger volume of scintillator located behind the opening 450 in the mask 448 rather than scattering outside the scintillator material. If desired, an additional layer of low-Z material (not shown) may be interposed between the cladding and the shielding layers so as to absorb secondary lead x-rays emitted by the mask 448. As will be clear to those of skill in the art, the detectors shown in FIGS. 14a–c have the improved efficiency of wider detectors with the higher resolution of narrower detectors. Similar masking can be applied to solid state detectors, such as shown in FIG. 2, resulting in similar advantages.

Figure 17:
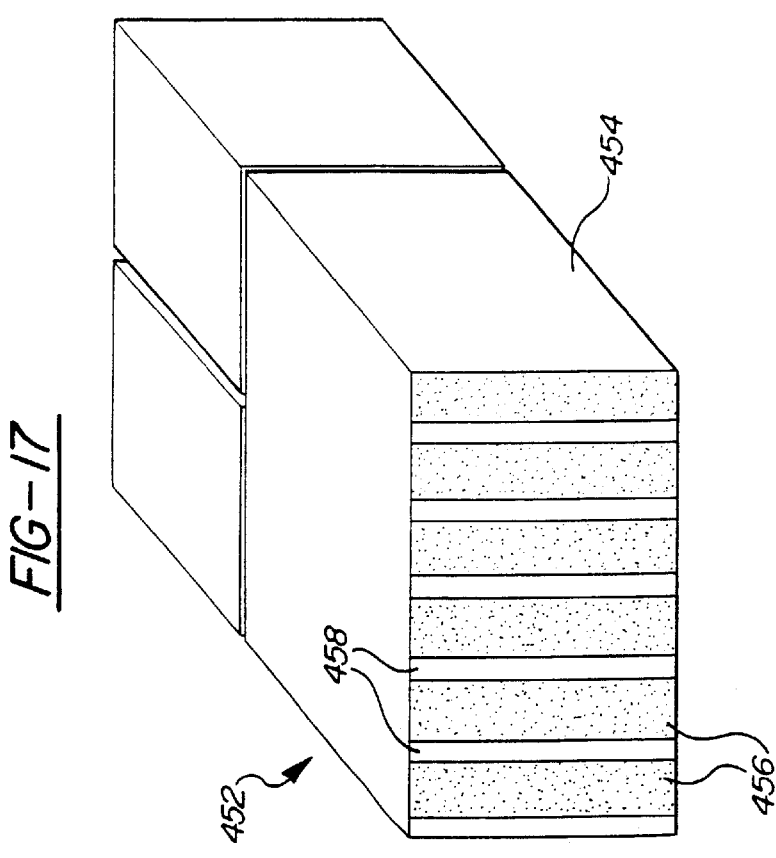
FIG. 17 is a perspective view of a two dimensional scintillator based detector having masking strips according to the present invention.

Referring to FIG. 17, a similar masking approach may be applied to a two dimensional piece of scintillation material to form a detector 452 with the benefits described above. Specifically, a piece of scintillation material 454 has mask of lead applied in strips 456 to its face. Narrow vertical openings 458 are left to allow entrance of photons aligned with the openings. Like with the embodiment of FIGS. 14a–14c, this give increased accuracy. Photodetectors 459 are positioned behind the scintillation material 454 and are capable, by means such as "Anger logic", of detecting where a pulse of light occurs. Because a portion of the face is masked, the electronics "knows" that the photon did not strike in the masked areas and can therefore more precisely pinpoint the location of the strike. The masking off of certain portions of the detector surface reduces, in effect, the positional uncertainty of a given pulse of light, thus permitting its position to be determined more accurately and precisely.

Figure 15:
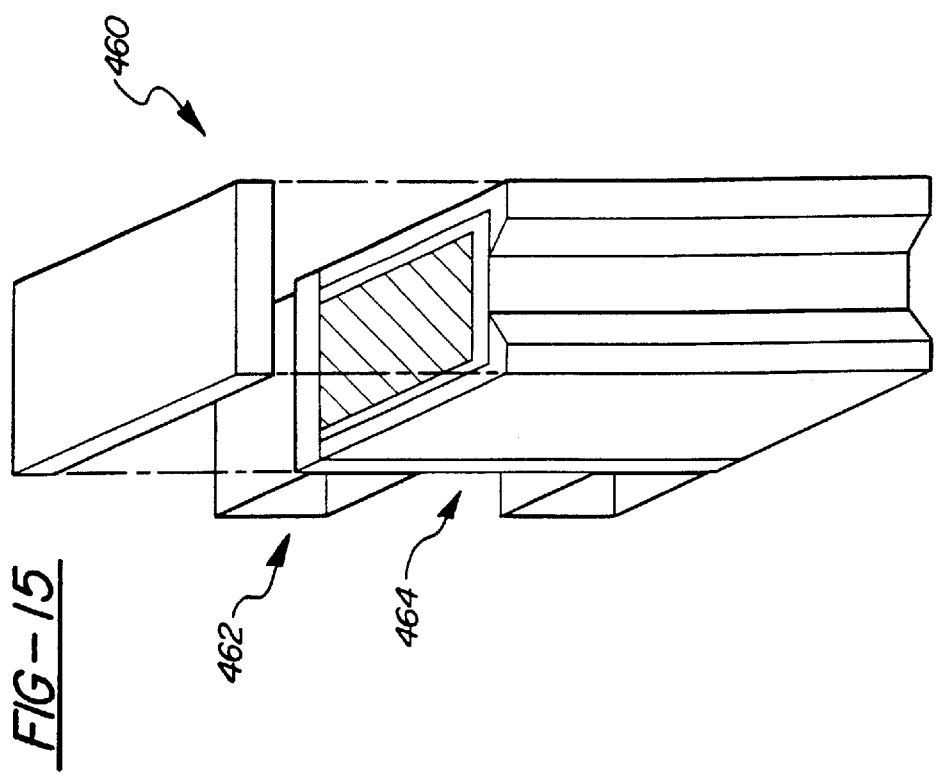
FIG. 15 is a perspective view showing construction details of a bar-shaped, masked detector module similar to FIG. 14a, but with photo-detectors placed along its rear face.

FIG. 15 shows details of construction of a bar-shaped, masked detector module 460 as described in the previous Figures but with the photo-detectors 462 attached at the rear face through use of optical coupling material 464. A similar masking configuration may be used with solid-state detector modules. As will be clear to those of skill in the art, photo-detectors of various types are somewhat costly. Therefore, it is desirable to reduce the number required. According to another embodiment of the present invention, a pair of optical fibers may be attached to each of the scintillation based detectors, with one fiber connected to each end of the detector. The fiber may be connected to the top and bottom or to the back face adjacent the top and bottom. The optical fibers may then be routed to a photomultiplier of the type have position sensitivity. These readily available multichannel photomultipliers are capable of providing distinct outputs for a multiplicity of locations across the face of an individual tube. Such a photomultiplier can then sense light pulses from a large number of optical fibers running from various detectors. In this way, the total number of photo detectors is reduced. A similar approach may be applied to two dimensional scintillation based detectors. Rather than using photodetectors mounted to the rear of the material, multiple optical fibers may be used to route the light to multichannel detectors.

As previously discussed, the pieces of scintillation material that form the core of a scintillation based detector are clad in a radiolucent, light reflecting material such as aluminum. This increases the brightness of the pulse of light as perceived by the light detectors. However, in some situations, this reflectivity may interfere with the ability of the light detectors to determine the longitudinal position where the photon struck the scintillation material. Therefore, it may be beneficial to reduce the reflectance of one or more surfaces of the scintillation material. For this purpose, the surface may be roughened prior to cladding, the cladding may be roughened in certain areas, or a lower reflectance coating may be applied to either the scintillation material or the cladding. Alternatively, it may be desirable to vary the reflectance along the length of the reflector. For example, a roughed strip on one surface of the scintillation material may vary in width along the length of the detector. The strip could be narrow in the center, so that reflectance remains high, and wider near the ends so that reflectance is reduced.

Figure 16:
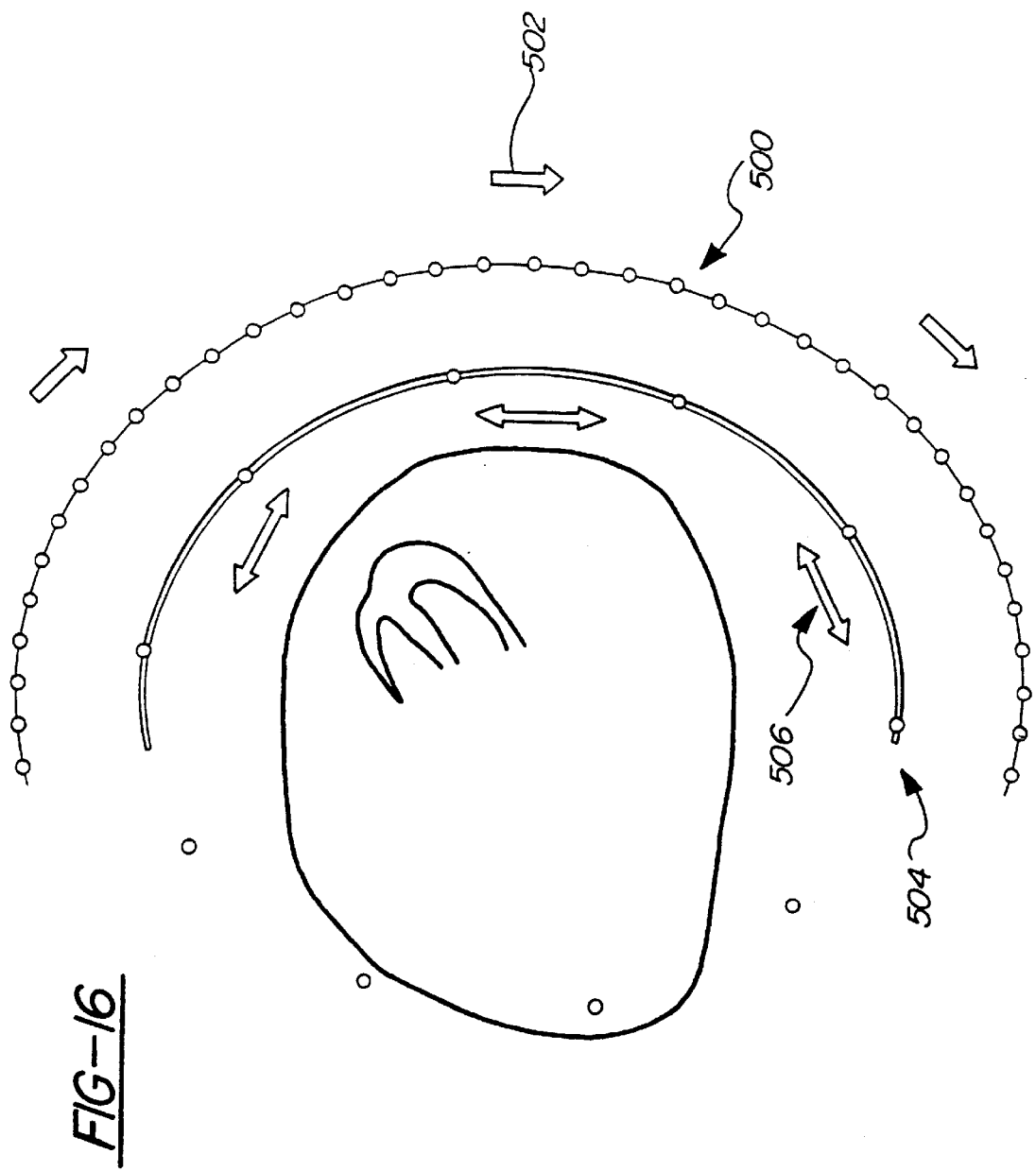
FIG. 16 is a diagrammatic representation of the directions of concurrent detector and aperture arc motion for one embodiment of the invention.

If the spacing of detector modules is sparse, gaps may be seen in the pattern of angular sampling provided by this system. The importance of such gaps depends on the number of angular "bins" of data obtained as the aperture arc moves. In addition, the significance of any artifacts caused by incomplete angular sampling depends on the clinical setting. If such artifacts are objectionable, this invention optionally provides for a means (FIG. 16) of rotation of the arc of detector modules 500 through a limited angular range 502, such motion occurring either continuously or in a limited number of discrete steps. The range of motion of the detector arc is equal to the spacing between detectors. At each step of detector motion, the aperture arc 504 is moved through its range of motion 506. In this manner, a full set of angular projections may be obtained with even sparse detector population.

As another alternative, a tomography system according to the present invention may be provided with a reduced number of detectors to reduce the cost of the system. This system would have either reduced resolution or would require an increased scan time. Later, the system may be upgraded by adding additional detectors at positions between the existing detectors.

Figure 18:
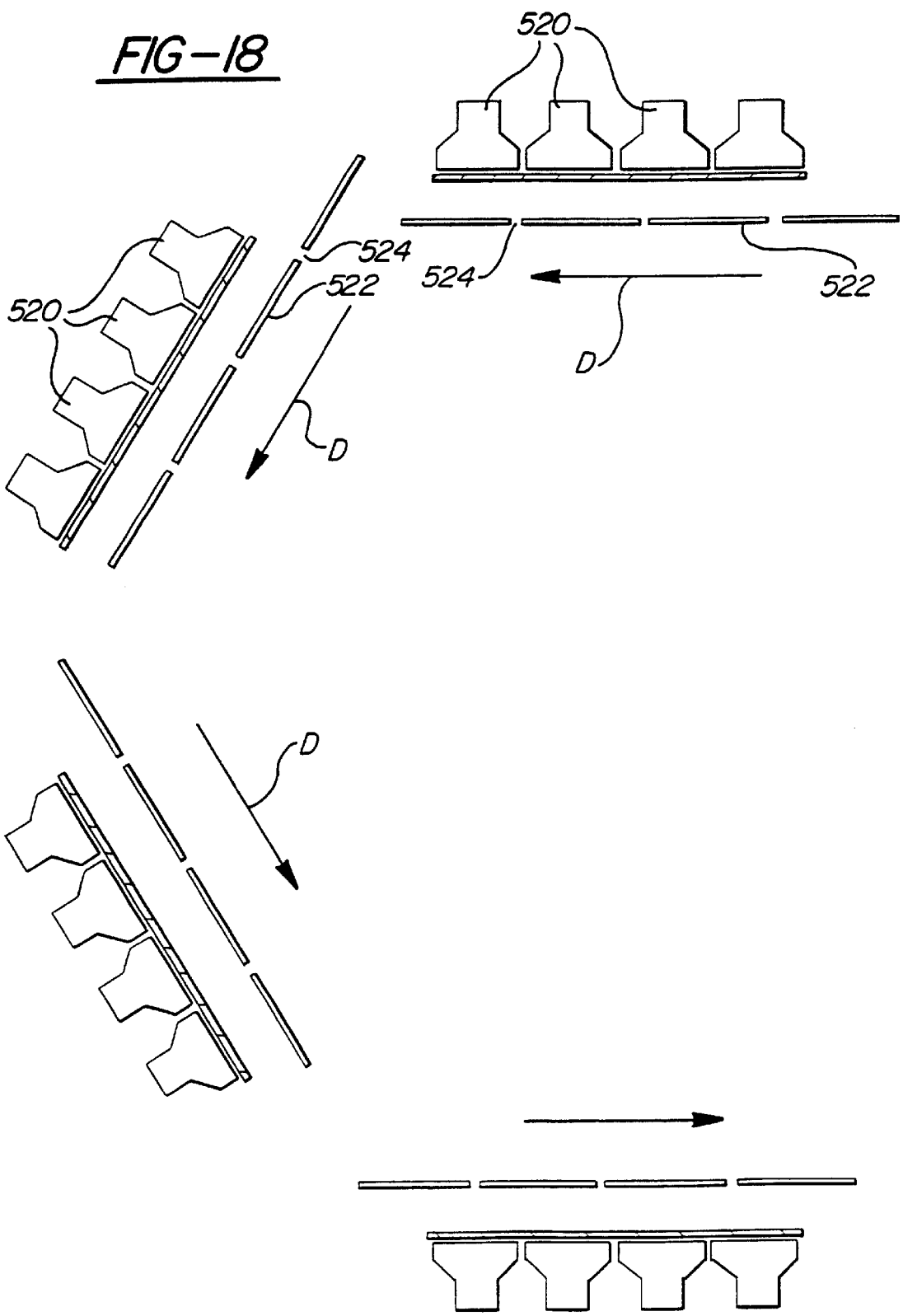
FIG. 18 is a top diagrammatic view of yet another embodiment of the present invention, which makes use of two dimensional detectors and linear blocking members.

The previously described embodiments of the present invention have specified that the detectors, the collimators, and the blocking member each be arcuate in shape. As will be clear to those of skill in the art, other shapes are also possible. For example, the detectors may be laid out in a rectangular or square arrangement. The blocking member and the collimators could be shaped likewise. As another example, sets of either strip or two dimensional detectors may be arranged in straight rows at various positions around the field of view. This approach is shown in FIG. 18 using two dimensional detectors 520. Each row of detectors 520 has a blocking member 522 in the form of a straight sheet positioned in front of it. The blocking member 522 has apertures, such as slots 524, defined through it and moves as shown by arrows D so that lines or response are swept across the field of view. Collimators, as discussed with other embodiments herein, may also be provided. As a further alternative, the detectors, either strip or two dimensional, may be arranged as shown in FIG. 18 and an arc or ring shaped blocking member may be used. This arrangement, or the arrangement of FIG. 18 may cover an arc between 180 and 360 degrees. In these embodiments, if two dimensional detectors are used, conventional large two dimensional detectors, as used in gamma cameras may be cut into several, preferably four, pieces to provide the smaller two dimensional detectors necessary for these embodiments. This reduces the total cost of components.

The previously discussed embodiments of the tomography system have been optimized for cardiac applications. However, the present invention is also highly applicable to scanning other portions of the body. Head and breast scans are two examples. For head scans, the imaging section completely surrounds a field of view sized for a head. The blocking member is an aperture ring and the collimators and detectors are concentric ring about the aperture ring. The imaging section may be positioned either horizontally or vertically. For breast scans, the system is similar to head scans with the imaging section completely surrounding the field of view. The imaging section preferably is positioned so that the opening is generally vertical. The patient is positioned such that the breast hangs into the opening during scanning.

Depending on the application, the system of the present invention may include other accessories. For example, in cardiac work, it may be desirable to stress the heart by having the patient perform an exercise. For this purpose, the system may include a bicycle ergometer that is either permanent or detachable. Also, the system may include an electrocardiogram and/or a built in cardiac defibrillator. Also, a intravenous infusion pump may be included or be attachable.

Other variations on the disclosed preferred embodiments will be clear to those of skill in the art. It is the following claims, including all equivalents, that define the scope of the present invention.

What is claimed is:

1. A single photon emission computed tomography system for producing multiple tomographic images of the type representing a three-dimensional distribution of a photon-emitting radioisotope, said system comprising:

a base including a patient support for supporting a patient such that a portion of the patient is located in a field of view, a longitudinal axis being defined through the field of view;

a generally arcuate detector assembly adjacent to the field of view, said detector assembly extending generally arcuately at least partially about the field of view between a first end and a second end, said first and second ends being spaced apart so as to define an entry opening to the field of view, the detector assembly comprising a plurality of photon-responsive detectors arranged along the arcuate detector assembly, each detector being operable to detect if a photon strikes the detector;

a collimating assembly including at least two spaced apart collimating vanes of photon-attenuating material, each of said vanes being disposed between said detectors and the field of view;

a generally arcuate photon-blocking member disposed between the field of view and said detectors, said blocking member having a plurality of aperture slots defined therethrough at intervals along said member for passage of photons aligned with said aperture slots, a line of response for each of said detectors being defined from said detector through the nearest of said aperture slots; and a displacement actuator operable to move said photon-blocking member relative to said detectors such that said aperture slots are displaced relative to said detectors and said lines of response are swept across at least a portion of the field of view.

2. The system according to claim 1, wherein said detectors each comprise an elongated strip with a central axis disposed generally parallel to the longitudinal axis, each of said detectors further including means to determine a position along the length of said elongated strip where a photon is detected.

3. The system according to claim 1, wherein said aperture slots are each generally parallel to the longitudinal axis.

4. The system according to claim 1, wherein said detector assembly extends over an arc of approximately 180 degrees.

5. The system according to claim 1, wherein said detector assembly extends over an arc between 180 and 360 degrees.

6. The system according to claim 1, wherein said detector assembly further comprises a housing for supporting said detectors, said housing being formed of photon attenuating material on the portions of the housing not directed toward the field of view.

7. The system according to claim 1, wherein said detectors and said photon-blocking member define concentric arcs.

8. The system according to claim 1, wherein each of said collimating vanes in said collimating assembly is in a plane generally perpendicular to the longitudinal axis.

9. The system according to claim 8, wherein said collimating vanes are disposed between said photon-blocking member and said detectors.

10. The system according to claim 1, wherein said collimating assembly further includes a radiolucent material disposed in the spaces between said collimating vanes.

11. The system according to claim 1, wherein the patient support supports the human patient such that a portion of the patient's torso is located in a field of view, the patient's torso extending generally vertically such that the patient's head is substantially higher than the patient's hips, the longitudinal axis being generally vertical.

12. The system according to claim 11, wherein said base comprises a chair-like structure having a generally horizontal bottom portion for supporting the patient's hips and a generally vertical back portion of supporting the patient's back.

13. The system according to claim 12, wherein said generally arcuate detector assembly is interconnected with said back portion of said base such that said assembly partially surrounds the patient's torso when the patient is seated on said bottom portion.

14. A single photon emission computed tomography system for producing multiple tomographic images of the type representing a three-dimensional distribution of a photon-emitting radioisotope, said system comprising:

a base including a patient support for supporting a patient such that a portion of the patient is located in a field of view, a longitudinal axis being defined through the field of view;

a generally arcuate detector assembly adjacent to the field of view, said detector assembly extending generally arcuately at least partially about the field of view between a first end and a second end, said first and second ends being spaced apart so as to define an entry opening to the field of view, the detector assembly comprising a plurality of photon-responsive detectors arranged along the arcuate detector assembly, each detector being operable to detect if a photon strikes the detector;

a collimating assembly including at least two spaced apart collimating vanes of photon-attenuating material, each of said vanes being disposed between said detectors and the field of view;

a generally arcuate photon-blocking member disposed between the field of view and said detectors, said blocking member having a plurality of aperture slots defined therethrough at intervals along said member for passage of photons aligned with said aperture slots, a line of response for each of said detectors being defined from said detector through the nearest of said aperture slots; and a displacement actuator operable to move said detectors relative to said photon-blocking member such that said detectors are displaced relative to said aperture slots and said lines of response are swept across at least a portion of the field of view.

15. The system according to claim 14, wherein said detectors each comprise an elongated strip with a central axis disposed generally parallel to the longitudinal axis, each of said detectors further including means to determine a position along the length of said elongated strip where a photon is detected.

16. The system according to claim 14, wherein said aperture slots are each generally parallel to the longitudinal axis.

17. The system according to claim 14, wherein said detector assembly extends over an arc of approximately 180 degrees.

18. The system according to claim 14, wherein said detector assembly extends over an arc between 180 and 360 degrees.

19. The system according to claim 14, wherein said detector assembly further comprises a housing for supporting said detectors, said housing being formed of photon attenuating material on the portions of the housing not directed toward the field of view.

20. The system according to claim 14, wherein said detectors and said photon-blocking member define concentric arcs.

21. The system according to claim 20, wherein each of said vanes is in a plane generally perpendicular to the longitudinal axis.

22. The system according to claim 21, wherein said collimating vanes are disposed between said photon-blocking member and said detectors.

23. The system according to claim 14, wherein said collimating assembly further comprises a radiolucent material disposed in the spaces between said vanes.

24. The system according to claim 16, wherein the patient support supports the human patient such that a portion of the patient's torso is located in a field of view, the patient's torso extending generally vertically such that the patient's head is substantially higher than the patient's hips, the longitudinal axis being generally vertical.

25. The system according to claim 24, wherein said base comprises a chair-like structure having a generally horizontal bottom portion for supporting the patient's hips and a generally vertical back portion of supporting the patient's back.

26. The system according to claim 25, wherein said generally arcuate detector assembly is interconnected with said back portion of said base such that said assembly partially surrounds the patient's torso when the patient is seated on said bottom portion.

* * * * *

UNITED STATES PATENT AND TRADEMARK OFFICE
CERTIFICATE OF CORRECTION

PATENT NO. : 6,504,157 B2
DATED : January 7, 2003
INVENTOR(S) : Juhi

It is certified that error appears in the above-identified patent and that said Letters Patent is hereby corrected as shown below:

Column 2,
Line 21, replace "othe" with -- the --.

Column 7,
Line 29, replace "detector" with -- dectectors --.

Column 10,
Line 34, replace "give" with -- gives --.
Line 58, replace "type have position" with -- type having position --.

Column 12,
Line 10, replace "are concentric ring" with -- are concentric rings --.
Line 25, replace "also, a" with -- Also an --.

Column 13,
Line 37, replace "portion of" with -- portion for --.

Column 14,
Line 38, replace "20" with -- 14 --.
Line 39, replace "said vanes" with -- said collimating vanes in said collimating assembly --.
Line 48, replace "claim 16" with -- claim 14 --.
Line 57, replace "portion of" with -- portion for --.

Signed and Sealed this

Fifth Day of August, 2003

JAMES E. ROGAN
*Director of the United States Patent and Trademark Office*